United States Patent [19]

Forster et al.

[11] 4,204,533
[45] May 27, 1980

[54] SURGICAL PLATE FOR HOLDING THE HAND AND THE FINGERS DURING HAND AND FINGER OPERATIONS

[76] Inventors: George Forster, Schlossmuhlendamm 8-10, 2100 Hamburg 90; Herbert Von Wettstein, Hammer Str. 38b, 2000 Hamburg 70, both of Fed. Rep. of Germany

[21] Appl. No.: 935,645

[22] Filed: Aug. 21, 1978

Related U.S. Application Data

[63] Continuation of Ser. No. 777,702, Mar. 15, 1977, abandoned.

[30] Foreign Application Priority Data

Apr. 1, 1976 [DE] Fed. Rep. of Germany ... 7610104[U]

[51] Int. Cl.² .............................................. A61F 13/00
[52] U.S. Cl. ...................................... 128/133; 128/77; 269/328
[58] Field of Search ................. 128/133, 26, 77, 87 A, 128/79, 303 R; 132/73

[56] References Cited

U.S. PATENT DOCUMENTS

| | | | |
|---|---|---|---|
| 1,585,861 | 5/1926 | Huff | 128/79 |
| 1,708,757 | 4/1929 | Freileweh | 128/87 A |

Primary Examiner—Lawrence W. Trapp
Attorney, Agent, or Firm—Staas & Halsey

[57] ABSTRACT

A surgical element for fixing the position of the hand and the fingers during an operation consisting of a plate that is configured as a hand with spread-apart fingers and elastic, removable rings positioned over some of the fingers of the patient and the fingers of the plate to secure the hand to the plate.

1 Claim, 3 Drawing Figures

U.S. Patent May 27, 1980 4,204,533
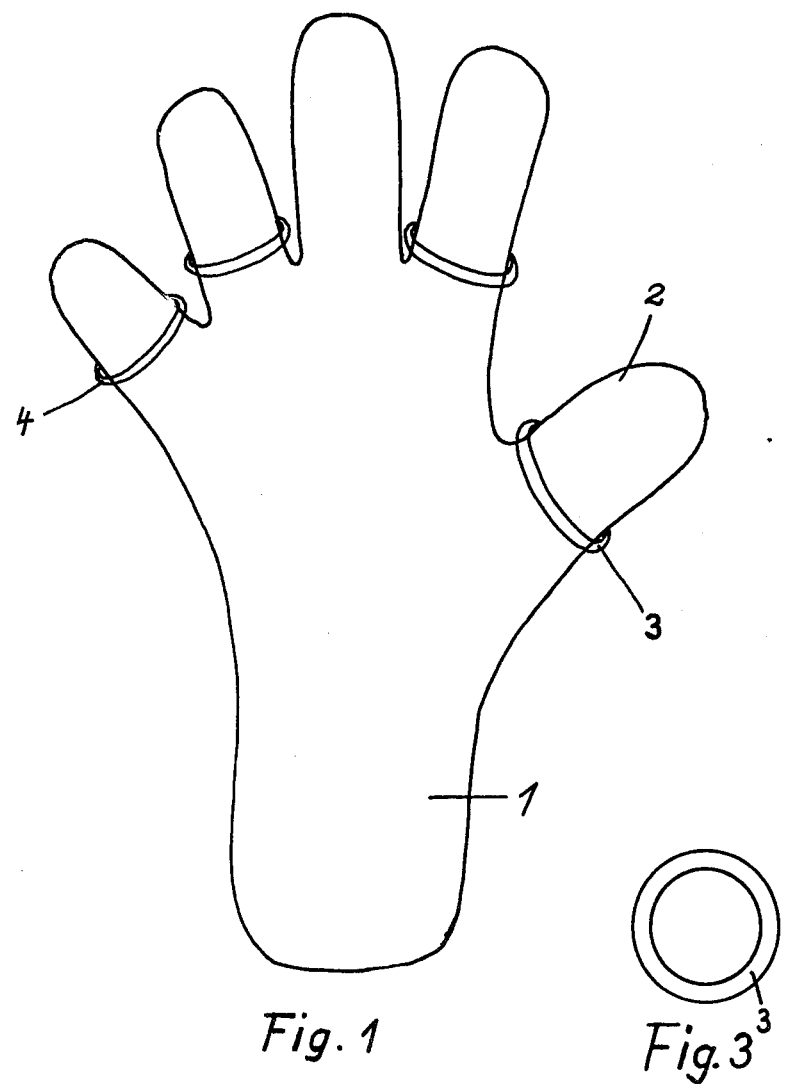
Fig. 1
Fig. 3
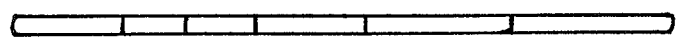
Fig. 2

SURGICAL PLATE FOR HOLDING THE HAND AND THE FINGERS DURING HAND AND FINGER OPERATIONS

This is a continuation of application Ser. No. 777,702 filed Mar. 15, 1977 now abandoned.

BACKGROUND AND SUMMARY OF INVENTION

The present invention relates to a surgical instrument for holding the hand and the fingers during operation. In the past, the hand during an operation has been fixed with a lead support whereby the thumb, index finger and small finger are held with straps made of the same material. After repeated use such straps are frequently broken and, moreover, because of the weight of the lead support it is not possible to conveniently move the support with the hand attached thereto during an operation.

The present invention is designed to affix the hand and fingers thereto with ease while permitting the plate to move with the hand during the operation. Moreover, with the present invention a long and useful life for the plate is assured. According to the invention as disclosed herein the plate has the shape of a hand with spread-out fingers, and elastic, movable rings are positioned over the fingers of the plate for the purpose of securing the fingers of the patient to the corresponding fingers of the plate. With the present invention all portions of the hand and the fingers are easily accessible to the surgeon. After the hand is positioned on the plate, and the elastic rings are positioned over the fingers of the patient, the plate and the hand may be moved thus permitting a variety of positions to be achieved and a greater mobility during the operation. The plate may consist of polypropylene and the movable elastic rings may consist of polyvinyl chloride. The "fixating" plate may be sterilized in accordance with known techniques, and the material of which the plate is constructed should be designed to resist iodine and chromium halogens and as well to bear high thermal and mechanical loads.

BRIEF DESCRIPTION OF THE DRAWINGS

FIG. 1 is a top plan view of the surgical plate of the present invention, illustrating several of the elastic rings positioned over the fingers and thumb;

FIG. 2 is a front elevational view of the surgical plate; and

FIG. 3 is a top plan view of one of the elastic rings.

DESCRIPTION OF THE PREFERRED EMBODIMENTS

The surgical plate of the present invention which is used to fix the position of the hand and the fingers during an operation consists of a plate 1 which is made of polypropylene and which is provided with fingers 2 positioned in the spread position. The removable, elastic rings 3 and 4 are positioned over the fingers 2 of the plate 1 and are made of polyvinyl chloride. The surgical fixation plate 1 is thus resistant to iodine and chromium halogens and may bear high thermal and mechanical loads, in addition to its capability of being sterilized in accordance with known techniques.

In carrying out an operation, the hand to be operated on is positioned on the plate 1 and then the elastic rings 3 and 4 are slipped over the corresponding fingers of the patient and the fingers 2 of the plate 1. The rings 3 and 4 thus fix the hand and the fingers firmly to the plate 1. As seen in FIG. 1, the ring 4 may be omitted from the finger to be operated on. In this case, the middle finger.

We claim:

1. A surgical element comprising:
   means for fixedly holding the position of a hand and fingers of a patient during an operation and yet permitting easy accessibility to the hand and fingers by the surgeon including;
   a plate in the shape of a hand and provided with spread-apart fingers, said plate being made of material means which is particularly resistant to iodine and chromium halogens and also can bear high thermal and mechanical loads to permit sterilization thereof; and
   elastic, removable rings positionable over all but one of the fingers of the patient and over the corresponding ones of said fingers of the plate.

* * * * *